United States Patent
Clarke et al.

(10) Patent No.: US 10,765,818 B2
(45) Date of Patent: Sep. 8, 2020

(54) DRY POWDER INHALER

(71) Applicant: VECTURA DELIVERY DEVICES LIMITED, Wiltshire (GB)

(72) Inventors: Roger Clarke, Cambridge (GB); Peter Wilson, Cambridge (GB)

(73) Assignee: Vectura Delivery Devices Limited, Wiltshire (GB)

( * ) Notice: Subject to any disclaimer, the term of this patent is extended or adjusted under 35 U.S.C. 154(b) by 542 days.

(21) Appl. No.: 15/528,922

(22) PCT Filed: Nov. 6, 2015

(86) PCT No.: PCT/EP2015/075982
§ 371 (c)(1),
(2) Date: May 23, 2017

(87) PCT Pub. No.: WO2016/083102
PCT Pub. Date: Jun. 2, 2016

(65) Prior Publication Data
US 2017/0326313 A1 Nov. 16, 2017

(30) Foreign Application Priority Data
Nov. 26, 2014 (EP) .................................... 14195012

(51) Int. Cl.
*A61M 15/00* (2006.01)
*A61K 9/00* (2006.01)

(52) U.S. Cl.
CPC .... *A61M 15/0045* (2013.01); *A61M 15/0023* (2014.02); *A61M 15/0031* (2014.02);
(Continued)

(58) Field of Classification Search
CPC .............. A61M 15/00; A61M 15/0001; A61M 15/0028; A61M 15/003; A61M 15/0031;
(Continued)

(56) References Cited

U.S. PATENT DOCUMENTS 5,622,166 A * 4/1997 Eisele ............... A61M 15/0045
128/203.12
5,881,719 A * 3/1999 Gottenauer ....... A61M 15/0045
128/203.15
(Continued)

FOREIGN PATENT DOCUMENTS

AU 2013201499 4/2013
BR PI0508549 8/2007
(Continued)

OTHER PUBLICATIONS

Translation of Chinese Office Action in App. No. 201580063748.9 dated Apr. 19, 2019.
(Continued)

*Primary Examiner* — Kendra D Carter
*Assistant Examiner* — Thomas W Greig
(74) *Attorney, Agent, or Firm* — Reed Smith LLP; Matthew S. Gibson; Ryan P. Cox

(57) ABSTRACT

A dry powder inhaler with a blister folding device can include a housing to receive a single blister containing a dose of medicament for inhalation by a user, and a mouthpiece through which a dose of medicament is inhaled by a user and a blister opening device. The blister opening device can include a blister support element for supporting a blister containing a dose of medicament for inhalation by a user, and a blister folding element co-operable with the blister support element. The blister folding element and the blister support element can be movable relative to each other between a first position, for insertion of the blister into or onto the blister support element, and a second, burst, position in which the blister folding element has co-operated with the blister support element.

20 Claims, 14 Drawing Sheets

Figure 1:
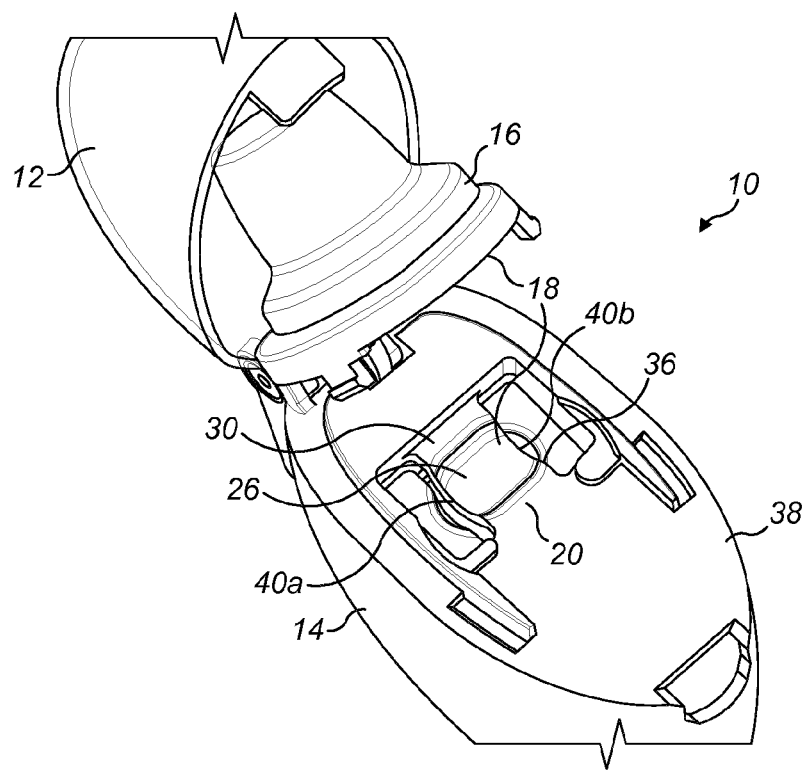

(52) U.S. Cl.
CPC ....... *A61M 15/0086* (2013.01); *A61K 9/0075* (2013.01); *A61M 15/0021* (2014.02); *A61M 15/0025* (2014.02); *A61M 15/0026* (2014.02); *A61M 15/0041* (2014.02); *A61M 2202/0007* (2013.01); *A61M 2202/0064* (2013.01); *A61M 2206/16* (2013.01)

(58) Field of Classification Search
CPC .......... A61M 15/0033; A61M 15/0035; A61M 15/0036; A61M 15/0038; A61M 15/004; A61M 15/0041
See application file for complete search history.

(56) References Cited

U.S. PATENT DOCUMENTS

| | | | |
|---|---|---|---|
| 6,810,872 B1 * | 11/2004 | Ohki | A61M 15/0045 |
| | | | 128/203.15 |
| 6,907,880 B1 | 6/2005 | Heckenmuller et al. | |
| 7,318,435 B2 * | 1/2008 | Pentafragas | A61M 15/0028 |
| | | | 128/203.15 |
| 8,561,608 B2 | 10/2013 | Chopard | |
| 8,739,785 B2 * | 6/2014 | Wright | A61M 15/0028 |
| | | | 128/203.15 |
| 2001/0029947 A1 | 10/2001 | Paboojian et al. | |
| 2001/0035184 A1 * | 11/2001 | Schuler | A61M 15/0028 |
| | | | 128/203.15 |
| 2003/0170183 A1 | 9/2003 | Staniforth | |
| 2004/0123864 A1 | 7/2004 | Hickey et al. | |
| 2009/0090362 A1 * | 4/2009 | Harmer | A61M 15/0045 |
| | | | 128/203.21 |
| 2010/0083962 A1 | 4/2010 | Von Schuckmann et al. | |
| 2010/0083963 A1 | 4/2010 | Wharton et al. | |
| 2010/0258118 A1 * | 10/2010 | Morton | A61K 9/0075 |
| | | | 128/203.15 |
| 2012/0037158 A1 * | 2/2012 | Wachtel | A61M 15/0045 |
| | | | 128/203.21 |
| 2012/0138055 A1 * | 6/2012 | Meliniotis | A61M 15/0045 |
| | | | 128/203.15 |
| 2015/0343159 A1 * | 12/2015 | Farr | A61M 15/0035 |
| | | | 128/203.15 |

FOREIGN PATENT DOCUMENTS

| | | | | |
|---|---|---|---|---|
| CN | 1950122 A | | 4/2007 | |
| CN | 101772361 A | | 7/2010 | |
| CN | 102438684 A | | 5/2012 | |
| DE | 102009041664 A1 | * | 3/2011 | ........ A61M 15/0028 |
| DE | 102010016549 A1 | * | 10/2011 | ........ A61M 15/0028 |
| EP | 2210638 | | 7/2010 | |
| EP | 1684834 | | 7/2011 | |
| JP | 2001-161788 A | | 6/2001 | |
| JP | 2007-533363 A | | 11/2007 | |
| JP | 2008-161696 A | | 7/2008 | |
| RU | 2009115659 | | 11/2010 | |
| WO | 2001026720 | | 4/2001 | |
| WO | 2003000325 | | 1/2003 | |
| WO | 2005087299 | | 9/2005 | |
| WO | 2005118034 | | 12/2005 | |
| WO | 20090152477 | | 12/2009 | |
| WO | 2010086285 | | 8/2010 | |
| WO | WO-2012004485 A2 | * | 1/2012 | ........ A61M 15/0028 |
| WO | 2014006135 | | 1/2014 | |
| WO | 2014106727 | | 7/2014 | |

OTHER PUBLICATIONS

International Search Report and Written Opinion of PCT/EP2015/075982 dated Feb. 9, 2016.
European Search Report of EP14195012 dated Mar. 12, 2015.

* cited by examiner

DRY POWDER INHALER

CROSS-SECTION TO RELATED APPLICATIONS

This application is a United States national stage of International Application No. PCT/EP2015/075982, filed Nov. 6, 2015, which was published as International Publication No. WO 2016/083102, and which claims benefit of European Patent Application No. 14195012.1, filed Nov. 26, 2014, the entire contents of which are hereby expressly incorporated herein by reference.

The present invention relates to a blister opening device for a unit dose dry powder inhalation device. In particular, it relates to a blister bursting device for popping or bursting open the foil lid of a blister that contains an individual dose of medicament for inhalation by a user of the inhalation device.

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have also been used to deliver drugs to the bloodstream via the lungs, thereby avoiding the need for hypodermic injections.

It is common for dry powder formulations to be prepackaged in blisters, each of which contains a single dose of powder which has been accurately and consistently measured. The blister protects each dose from the ingress of moisture and penetration of gases such as oxygen in addition to shielding the dose from light and UV radiation, all of which can have a detrimental effect on the medicament and on the operation of an inhaler used to deliver the medicament to a patient.

A blister pack generally comprises a base having one or more spaced apart cavities defining blisters to receive individual doses of medicament and a lid in the form of a generally planar sheet that is sealed to the base except in the region of the cavities. The base material is typically a laminate comprising a polymer layer in contact with the drug, a soft tempered aluminium layer and an external polymer layer. The aluminium provides the moisture and oxygen barrier, whilst the polymer aids adhesion of the aluminium to the heat seal lacquer and provides a relatively inert layer in contact with the drug. Soft tempered aluminium is ductile so that it can be "cold formed" into a blister shape. It is typically 45 µm thick. The outer polymer layer provides additional strength and toughness to the laminate.

The lid material is typically a laminate comprising a heat seal lacquer, a hard rolled aluminium layer and an external lacquer layer. The heat seal lacquer layer bonds to the polymer layer of the base foil laminate during heat-sealing to provide a seal around the top of the blister cavity. The hard temper foil is relatively frangible to enable it to be pierced easily by a piercing element forming part of an inhalation device, to create one or more openings in the lid. These openings enable air or gas to flow through the blister, thereby entraining the dry powder and causing it to be removed from the blister. The powder can then be deagglomerated to form a respirable cloud and made available for inhalation by the user.

Inhalation devices that receive a blister pack or strip of blisters are known. Actuation of the device causes a mechanism to index and pierce a blister so that when the device is used, air is drawn through the blister entraining the dose, which is then carried out of the blister through the device and via the patient's airway down into the lungs. One such device is known from one of the Applicant's own European patent No. 1684834B1.

The airflow can be created by inhalation of the user. Such inhaler devices are generally known as passive devices. Alternatively, the inhaler may include a source of energy such as a mechanical pump or canister of pressurised gas to generate pressure or suction. The air or gas flow in these active devices can potentially be greater than that in a passive device, and more repeatable. This can give better and more consistent blister emptying.

Hitherto, much development work has been focused on piercing as a mode of blister opening. It is now well understood that it is difficult to control the size and configuration of the opening in a blister lid caused by piercing because the foil may not always tear or burst in a consistent way. Furthermore, the means by which the blister is pierced is of critical importance in the performance of a dry powder inhalation device.

It is common for problems to occur in dry powder inhalers that use piercers as means for opening blisters because, when the lid is pierced, foil flaps are formed that are pushed into the blister. These can either trap powder in the blister or obscure the opening. It will be appreciated that it is beneficial to form a large opening in the blister lid to enable a sufficient flow of air through the blister, and to enable the removal of agglomerates that may have formed in the powder during storage. However, a large opening in the blister means that the foil flaps are large and so are more likely to trap powder and hinder airflow. Furthermore, more powder may be trapped depending upon the orientation in which the device is being held when piercing takes place.

Trapped powder and a hindered airflow are the focus of WO2014/006135 from Glaxo Group Limited. It discloses a dry powder inhaler for receiving a single blister onto a blister seat. The inhaler housing is made up of a base and a lid which are pivotable relative to one another between open and closed positions, the lid supporting a punch and the base containing the aforementioned blister seat. The punch comprises an upstream blade and a downstream blade, each blade having a curved free cutting edge.

In use, the housing lid is moved from the open position, in which a blister may be placed on the blister seat, to the closed position, in which it abuts the housing base. In doing so, two apertures are created in the lid material. Once the initial piercing of the lid has taken place, and this occurs sequentially, flaps are formed in the lid material as the user continues to close the lid against the housing base. A final movement of the lid relative to the housing base causes the piercing blades to further enlarge the apertures formed in the lid.

In this prior art inhaler, the foil flaps are unusually considered advantageous as, together with an annular overhang about the blister bowl created during the opening process, they create a torturous flow path for the powder-laden airflow to follow as it exits the blister bowl. This torturous flow path is desirable because it assists with powder deagglomeration before inhalation.

In contrast to WO2014/006135, the present invention seeks to provide a blister opening device that ensures a smooth flow of air through an opened blister and avoids potentially expensive powder becoming trapped behind foil flaps created in the blister lid, which traditionally occurs when a blister lid is opened by piercing.

According to a first aspect of the invention, there is provided a dry powder inhaler comprising a housing to receive a single blister containing a dose of medicament for inhalation by a user, said blister comprising a blister lid attached to a blister bowl, a mouthpiece through which a dose of medicament is inhaled by a user and a blister opening device, the blister opening device comprising a blister support element for supporting a blister containing a dose of medicament for inhalation by a user, and a blister folding element co-operable with the blister support element, the blister folding element and the blister support element being movable relative to each other between a first position, for insertion of said blister into or onto the blister support element, and a second, burst, position in which the blister folding element has co-operated with the blister support element, movement from the first position to the second position causing two spaced apart portions of said blister to each fold relative to the remainder of the blister along a respective fold line and against the blister support element to produce two spaced apart openings, each opening extending along the circumference of the blister bowl, beginning and terminating at points located on the fold line such that, when a user inhales through the mouthpiece, an airflow through the blister via the two openings is generated to entrain the dose contained therein and carry it out of the blister and via the mouthpiece into the user's airway.

The key advantage of this invention is that when the blister is burst open, two unobstructed openings are created. This facilitates a rapid and unhindered exit of powder from the blister, which improves the emitted dose of the inhaler. This mode of opening blisters is particularly useful for spray dried formulations and biologics, which currently represent the cutting edge of pharmaceutical research. Such powders can be expensive and a minimal retention of powder within the blister bowl after opening is highly desirable.

Preferably, the blister folding element and the blister support element are pivotally connected to each other about a pivotal axis.

Preferably, the blister support element is arranged in or provided by an upper surface of the housing.

Optionally, the blister support element comprises a blister seat to support a blister bowl and a blister support surface to support the periphery of a blister surrounding said blister bowl.

The blister seat may comprise a central portion which has a truncated oval shape, each fold line being one edge of truncation.

The central portion may be suspended across a void or recess. Alternative arrangements may be possible, provided that there is space into which the blister can fold. The central portion and the void are a visual cue to the user that this is the place where the blister should be placed or inserted.

The blister seat may further comprise two depressible end portions adjacent to and either side of the central portion. The depressible portions help to eject the opened blister from the blister support element once the blister folding element is returned to its first position.

The depressible portions may be provided by a moveable support arm in the housing. The moveable arm may be pivotally mounted to the inside of the housing, and biased into its natural, resting position (i.e. un-depressed) using a spring. To clarify, in the resting position, the depressible end portions sit in the same plane as the central portion; the blister seat appears like a single surface. Alternatively, the moveable arm may be linearly moveable, and driven into the resting position by a small piston and cylinder type arrangement.

Optionally, the blister seat is configured such that the fold lines are of different lengths.

In one embodiment, a longitudinal extent of the blister seat is arranged in parallel with the pivotal axis. In an alternative embodiment, the longitudinal extent of the blister seat is arranged perpendicularly to the pivotal axis. In such an embodiment, the blister seat may be configured such that the fold line closest to the pivotal axis is longer than the fold line furthest away from said pivotal axis. The advantage of this particular arrangement is that two different sized openings can be created, if desired. Ideally, the larger of the two openings forms an outlet from the blister for powder entrained in an airflow.

Preferably, the blister folding element comprises at least one pair of spaced apart fold members receivable into the blister support element, the or each pair of fold members extending from a fold support structure. The fold members may be elongate.

The blister folding element may comprise two pairs of said spaced apart fold members, the second pair of spaced apart fold members being separated from the first said pair of spaced apart fold members by a distance greater than the length of the central portion of the blister seat.

In one embodiment, a first pair of said fold members is longer than a second pair of said fold members. This is particularly useful when the blister folding element is pivotable relative to the blister support element. Without the difference in length, the pair of fold members nearest the pivotal axis would ordinarily strike the blister lid fractionally earlier than the pair of fold members furthest away from the pivotal axis. With the difference in length, both openings can be created simultaneously.

A free end of each fold member may be bevelled. This shaping helps the applied folding pressure be transmitted gradually to the blister as the blister folding element moves from the first to the second position, resulting in a more controlled formation of the openings. Bevelled ends help to reduce the overall opening force required of the user.

The fold support structure may be adapted to provide a bypass air conduit for the flow of clean air over the burst blister when the blister folding element is in the second position. Additional clean air through the inhaler during inhalation reduces the inhalation resistance experienced by the user, making the inhaler suitable for use by patients with severe and chronic lung conditions such as asthma and COPD.

The blister opening device may further comprise a stress concentrating means to create a stress concentration in the lid of the blister prior to the blister being folded. This facilitates a more precise creation of an opening by providing a starting point for tear initiation. It also increases the predictability of the location of the source of the opening.

Preferably, the stress concentrating means comprises a piercing head and two piercing teeth depending therefrom. Additionally or alternatively, the stress concentrating means may comprise a knurled finish on the lid of the blister, score lines (e.g. laser scoring) or an indentation.

The stress concentrating means may be releasably engageable with the blister folding element so as to be moveable between an engaged position when the blister folding element is in the first position, and a released, retracted, position when the blister folding element is in the second, burst, position.

The piercing head may be arcuate. Preferably, the piercing head is curved to match the profile of the blister lid and the shape of the blister lid is only changed by the blister folding element The blister bowl support seat/surface may comprise a raised feature which causes the blister bowl to be indented when the blister opening device is reaching the closed, second position. By placing an indentation in the blister bowl, this pressurises the internal contents of the sealed blister just prior to opening which helps the lid of the blister to pop open during the opening process. The indentation may be a dimple or a convex channel extending along the length of the blister bowl.

Preferably, the blister or just the lid foil is curved about its longitudinal extent. Alternatively, the blister or just the lid foil is curved about its lateral extent. When used with a curved blister (or lid foil), an arcuate piercing head helps retain the shape (and therefore pre-tensioning) of the blister (or lid) during the pre-folding, piercing stage.

Preferably, the mouthpiece is pivotally connected to the housing. In such an arrangement, the blister folding element may depend from an underside of the mouthpiece.

Preferably, the dry powder inhaler further comprises a cyclone chamber within the mouthpiece, the chamber having an inlet at one end for the flow of drug laden air into the chamber from a burst blister and an outlet at its opposite end for the flow of drug laden air out of the mouthpiece and into a patient's airway. Ideally, the chamber has a longitudinal axis that extends between the inlet and the outlet.

Cyclone chambers, also known as deagglomeration chambers, help to break up large agglomerates formed during the blister filling process and subsequent storage. Agglomerates are broken up by impact or collision with the internal surfaces of the cyclone chamber. Agglomeration formation is exacerbated in particularly cohesive formulations. Spray dried formulations and biologics have been found to be cohesive by nature too. A cyclone chamber is particularly important for use in combination with this mode of opening blisters, since the inhaler is intended to be used to dispense spray dried formulations and biologics.

Additionally, cyclone separation using a cyclone chamber is a common method of removing particulates from an air stream. As the air flows in a rotating pattern, large agglomerates have too much inertia to follow the tight curve of the air stream and therefore impact the wall of the cyclone chamber.

The cyclone geometry and flow rate determine the agglomerate size which will remain in the cyclone. No two formulations have the same properties and therefore the size of the cyclone chamber needs to be designed individually for each formulation.

Optionally, the chamber comprises at least one bypass air inlet for the flow of clean air into the chamber to interact with the drug laden air flowing between the inlet and the outlet. Preferably, the bypass air inlet(s) meets the chamber at a tangent so that a cyclonic airflow is generated from clean air around the drug laden airflow. Agglomerates are formed due to cohesive forces between particles, but these forces also occur between particles and surfaces. Testing has shown that the deposition of fine particles on surfaces is a significant risk and with a biologic compound, the retention of powder in the device could lead to complications. Creating a cyclonic airflow reduces this risk.

Preferably, the or each bypass air inlet is arranged at or near the chamber outlet.

The longitudinal axis of the chamber may be arranged at an acute angle relative to the plane of the blister seat.

The chamber may comprise a spiraled floor to encourage a swirling airflow between the inlet and the outlet of the chamber.

According to a second aspect of the invention, there is provided a dry powder inhaler comprising a housing for receiving one or more blisters each containing a dose of medicament for inhalation by a user, a mouthpiece through which said dose of medicament is inhaled by a user, a blister opening device, and a cyclone chamber in communication with the mouthpiece, the chamber having an inlet at one end for the flow of drug laden air into the chamber from an opened blister and an outlet at its opposite end for the flow of drug laden air out of the mouthpiece and into a patient's airway, wherein the chamber has a spiraled floor at or proximate to the chamber inlet to disrupt the airflow flowing from the opened blister.

According to a third aspect of the invention, there is provided a dry powder inhaler comprising a housing for receiving one or more blisters each containing a dose of medicament for inhalation by a user, a mouthpiece through which said dose of medicament is inhaled by a user, a blister opening device, and a cyclone chamber in communication with the mouthpiece, the chamber having an inlet at one end for the flow of drug laden air into the chamber from an opened blister and an outlet at its opposite end for the flow of drug laden air out of the mouthpiece and into a patient's airway, the chamber further comprising at least one bypass air inlet for the flow of clean air into the chamber to interact with the drug laden air flowing between the inlet and the outlet, wherein the or each bypass air inlet is arranged at or near the chamber outlet. Preferably, the bypass air inlet(s) meets the chamber at a tangent.

Embodiments of the invention will now be described, by way of example only, with reference to the accompanying drawings, in which:—

FIG. 1 is a perspective view of an inhaler according to a first embodiment of the invention, with the blister folding element in the first position to reveal the blister support element;

FIG. 2 is an alternative perspective view of the inhaler of FIG. 1, showing the blister folding element;

FIG. 3 is a perspective view of a demonstration rig, with a blister placed onto the blister seat and the blister folding element in the first position;

FIG. 4 is a perspective view of the demonstration rig of FIG. 3 after the blister has been burst, and with the blister folding element back in the first position once more;

FIG. 5 is a perspective view of a second embodiment of the inhaler, with the cap closed;

FIG. 6 is a perspective view of the inhaler of FIG. 5, with the cap open and the blister folding element in the first position, ready for placement of a blister onto the blister support element;

FIG. 7 is a partial cross-sectional view through the side of the inhaler of FIG. 6;

FIG. 8 is a perspective view of the inhaler of FIG. 5, with the cap open and the blister folding element in the second position, ready for inhalation by a user;

FIG. 9 is a cross-sectional view through the side of the inhaler of FIG. 8;

FIG. 10 is a partial perspective cross-sectional view through the side of the inhaler of FIG. 8;

FIGS. 11 A to E show a cross-sectional side view of a demonstration rig operating in a sequence of steps to achieve blister folding in accordance with the invention, and shows in particular the stress concentrating means;

FIGS. 12 A to D show a perspective view of the demonstration rig of FIG. 15 in a shortened sequence of steps;

FIGS. 13 A to C illustrates the step-by-step formation of two openings in a curved blister;

FIG. 14 shows a side elevation view of a stress concentrating means which has an arcuate lower surface to follow the surface of a curved blister;

Figure 15A:
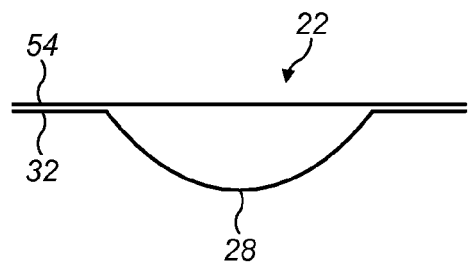
Figure 15B:
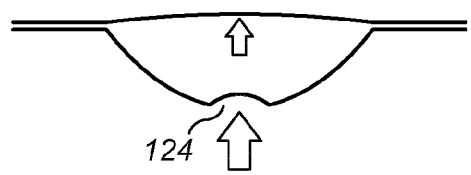
Figure 15C:
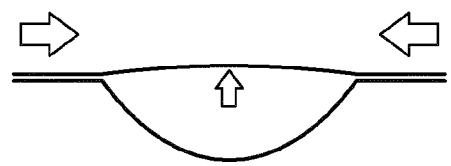
Figure 16A:
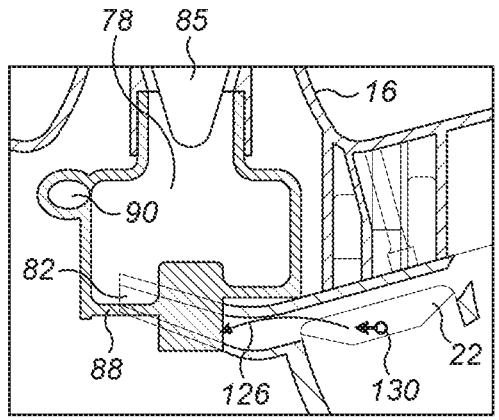
Figure 16B:
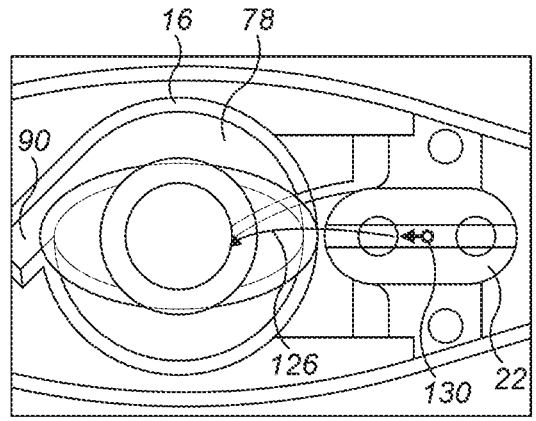

FIGS. 15 A to C are cross-sectional side views of an unmodified blister, a blister with a strengthening rib, and a blister with a pre-tensioned blister lid respectively, FIGS. 16A and 16B are cross-sectional side views of the chamber and the pierced blister, used to indicate the travel of a typical large particle/agglomerate through cyclonic airflow, with the 'A' figures being cross-sectional side views and the 'B' figures being corresponding plan views with hidden details; and FIGS. 17A and 17B, 18A and 18B, 19A and 19B, 20A and 20B, 21A and 21B, 22A and 22B, 23A and 23B are all progressions of FIGS. 16A and 16B.

A first embodiment of the inhaler will now be described with reference to FIGS. 1 to 4. A unit dose dry powder inhaler is indicated generally at 10. The inhaler comprises a cap 12, a housing 14 to which is pivotally mounted a mouthpiece 16 and a blister opening device 18.

The cap 12 is hinged to the top edge of the housing 14 and is pivotable between a closed position and an open position. The cap 12 completely covers and protects the mouthpiece 16 when closed and prevents contamination thereof or the possible ingress of dirt into the housing 14 which could otherwise be inhaled when the device is used.

The blister opening device 18 comprises a blister support element 20 for supporting a portion of a blister 22 containing a dose of medicament for inhalation by a user, and a blister folding element 24 which is co-operable with the blister support element 20. The blister folding element 24 and the blister support element 20 are moveable relative to each other between a first position for insertion of a blister 22 into or onto the blister support element 20 as indicated in FIG. 1, and a second position in which the blister folding element 24 has co-operated with the blister support element 20. In the second position, the blister 22 has been burst open.

The blister support element 20 is incorporated within the housing 14. The blister support element 20 comprises a blister seat 26 for receiving a portion of a blister bowl 28 (FIG. 15A) and a blister support surface 30 to support the periphery 32 of a blister surrounding said blister bowl 28. The blister seat 26 has a truncated oval shape. The blister seat 26 is suspended within a first aperture 34, across a void 36 in communication with the interior of the housing 14. The first aperture 34 is set into an upper surface 38 of the housing 14.

This configuration of blister seat 26 is intended for use with generally oval shaped blister bowls. In an untruncated state, the blister seat 26 would fully support an oval blister bowl 28. However, in a truncated state, only the middle portion of the blister bowl 28 is supported by the truncated blister seat 26, on central portion 26a, whilst the two end portions of the blister bowl 28 are unsupported. The two edges of truncation 40a, 40b of the blister seat 26 provide pre-determined fold lines, against which a blister 22 can be folded.

It is envisaged that other configurations of blister seat could be used for use with correspondingly shaped blister bowls, for example rectangular or circular blister bowls, provided that they too are truncated. It is also envisaged that the blister seat could be truncated along one edge only, not two as depicted in the illustrative embodiment. This configuration would produce only one opening in the burst blister.

It should be noted that the first aperture 34 could alternatively open into a void in the housing 14 and not a recess with a central hole as shown in FIG. 1.

Figure 2:
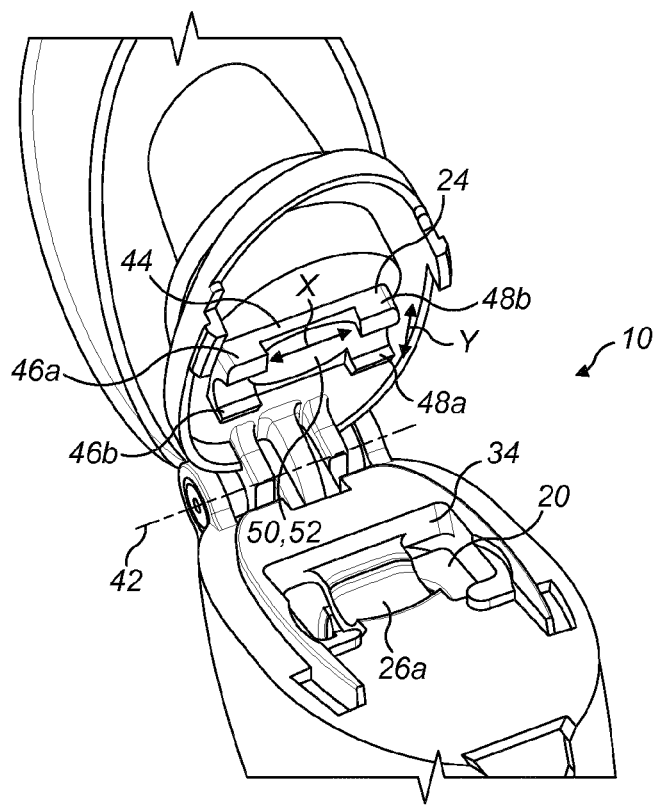

As best seen in FIG. 2, the blister folding element 24 is mounted to an underside of the mouthpiece 16. The mouthpiece 16 and the blister folding element 24 are pivotable relative to the housing 14 (and therefore the blister support element 20) about a pivotal axis 42.

The blister folding element 24 comprises a fold support structure 44 and two pairs of spaced apart fold members 46a, 46b, 48a, 48b extending from the fold support structure 44. In this example, the fold support structure 44 is rectangular. The fold support structure 44 has a similar general configuration (i.e. shape and size) to the first aperture 34 of the blister support element 20 such that the blister folding element 24 is at least partially receivable into the blister support element 20. An oval second aperture 50 is provided in the fold support structure 44. This second aperture 50 provides a void 52 into which a lid 54 of the blister 22 curves during the opening process and need not be oval.

By way of example only, each fold member 46a, 46b, 48a, 48b is a stubby square block, and there is one fold member 46a, 46b, 48a, 48b located in one corner of the rectangular fold support structure 44. The first said pair of spaced apart fold members 46a, 46b is separated from the second said pair of spaced apart fold members 48a, 48b by a distance greater than the length of the central portion 26a of the blister seat 26. The two pairs of fold members 46a and 46b, 48a and 48b are spaced apart by a distance X that influences the height of the opening 56a, 56b in the burst blister 22. Distance X can be reduced down to a minimum, below which the blister 22 will collapse and no openings 56a, 56b will form during folding.

Each pair of fold members 46a and 46b, 48a and 48b has two fold members that are spaced apart from each other by a distance Y that restricts the breadth (or it could equally be considered to be the length) of the resultant openings in the burst blister 22. The combination of distances X and Y determine the area of the opening 56a, 56b in the burst blister 22.

In this particular embodiment, the two fold lines are of the same length since the truncation edges 40a, 40b are of the same length. This produces two openings 56a, 56b of the same area in the resultant burst blister 22 because the distance of each fold line from the mid-point of the blister 22 is the same. Alternatively, the two fold lines (i.e. truncation edges 40a, 40b) may be of different lengths in order to create two differently sized openings 56a, 56b. Two differently sized openings 56a, 56b may also be created when the distance from the mid-point of the blister 22 for each fold line is different. Alternatively, a combination of varying the distance between the mid-point (X/2) and each fold line, and also the breadth (Y) of each fold line could be used to create openings 56a, 56b with different areas.

The blister folding element 24 does not include any sharp edges or points. Thus contact with the blister by the blister folding element 24 is solely by folding; no cutting, slicing or piercing of the blister is caused by the blister folding element 24.

Figure 3:
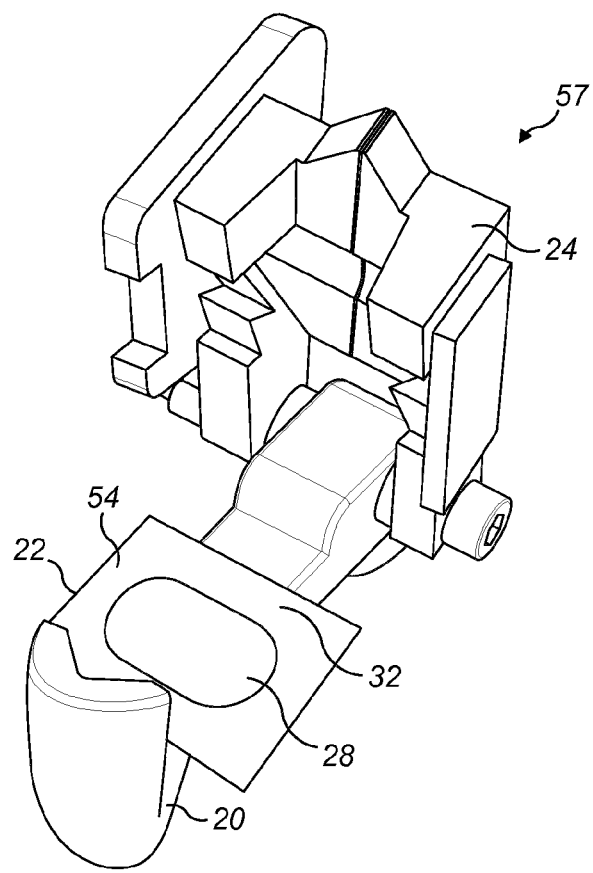
Figure 4:
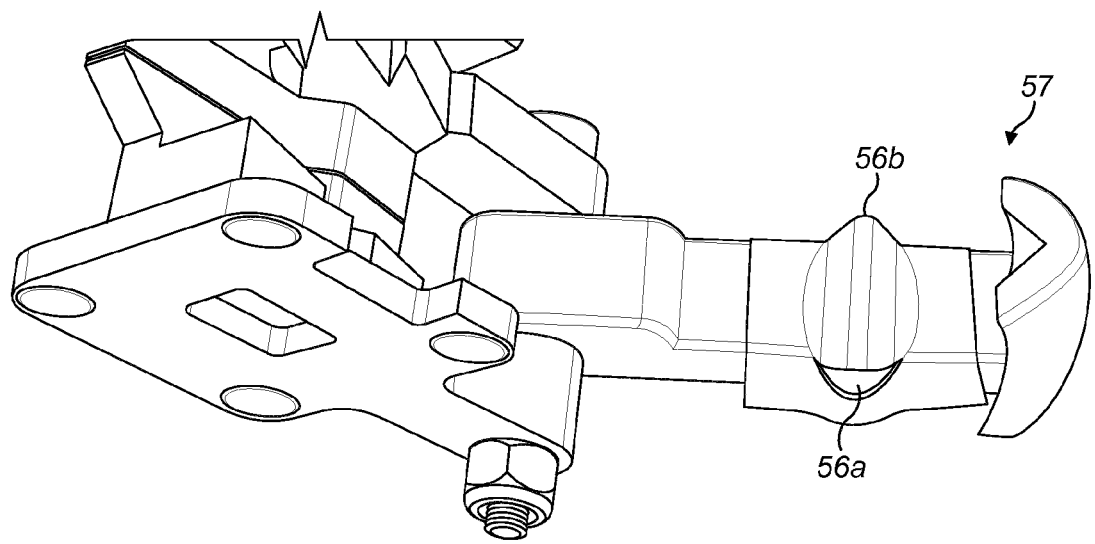

In use, as demonstrated by the demonstration rig 57 in FIGS. 3 and 4, when the blister folding element 24 is in the first position, a blister 22 is placed onto the central portion 26a of the blister seat 26. To move the blister folding element 24 from the first position into the second position, the blister folding element 24 is pivoted relative to the blister support element 20. As the blister folding element 24 moves closer and closer to the blister support element 20, the fold members 46a, 46b, 48a, 48b initially make contact with the unsupported portions of the blister, either side of the central portion 26a of the blister seat 26. The fold members 46a, 46b, 48a, 48b pass either side of and adjacent to the central portion 26a, pressing against and subsequently folding the unsupported portions of the blister 22 during this travel. Each of the two unsupported portions of the blister 22 collapses and folds against a truncated edge 40a, 40b of the central portion 26a of the blister seat 26 along a respective fold line. Since the blister bowl 28 of the blister is oval shaped in this example, the blister lid begins to separate from the blister bowl 28 at the pointed ends of the blister 22. Consequently, two openings 56a, 56b are formed, one at each end of the blister bowl 28. In use, one of the openings 56a will act as an airflow inlet into the burst blister 22, whilst the other opening 56b will act as an airflow outlet for powder laden air traveling from the burst blister 22.

Each opening 56a, 56b begins as a very small hole and rapidly increases in size as the tear between the blister lid 54 and the blister bowl 28 travels, following the line of the circumference of the blister bowl 28. The tear is confined between two points, each point being positioned on the fold line. The opening 56a, 56b is thus defined as extending along the circumference of the blister bowl 28, beginning and terminating at points located on the fold line.

The opening 56a, 56b is enlarged to its final configuration when the lidding material curves upwards during the final stages of opening 56a, 56b formation. This curvature is caused by the upper forming surfaces folding across the rounded bowl 28 edges. The curved blister bowl 28 is relatively strong compared to the flat foil surface of the blister lid 54; therefore the blister bowl 28 retains its shape and causes the perimeter foil to be curved around it. The flat perimeter and lid foil is 'shorter' than the curved edge it is being folded around, therefore the sides of the blister 22 must move closer together resulting in the lid foil being curved upwards. As the blister lid 54 pops upwardly, the blister bowl 28 below is left intact and largely unaltered in shape.

In the second position, the mouthpiece 16 and the blister folding element 24 lie generally against the upper surface 38 of the housing 14. The fold support structure 44 of the blister folding element 24 lies in a plane parallel to that of the first aperture 34 and is spaced apart from the blister support surface 30. This spacing 58 or gap provides a channel for a secondary airflow in which fresh air is able to bypass the burst blister 22. This secondary airflow supplements the primary airflow, which is through the burst blister and acts to entrain and evacuate powder contained therewithin. This will be explained in more detail with reference to the second embodiment.

A second embodiment of the invention will now be described with reference to FIGS. 5 to 18 and is indicated generally at 60. Similar features have been given the same reference numerals as in the previous figures and a detailed description has been omitted.

Figure 5:
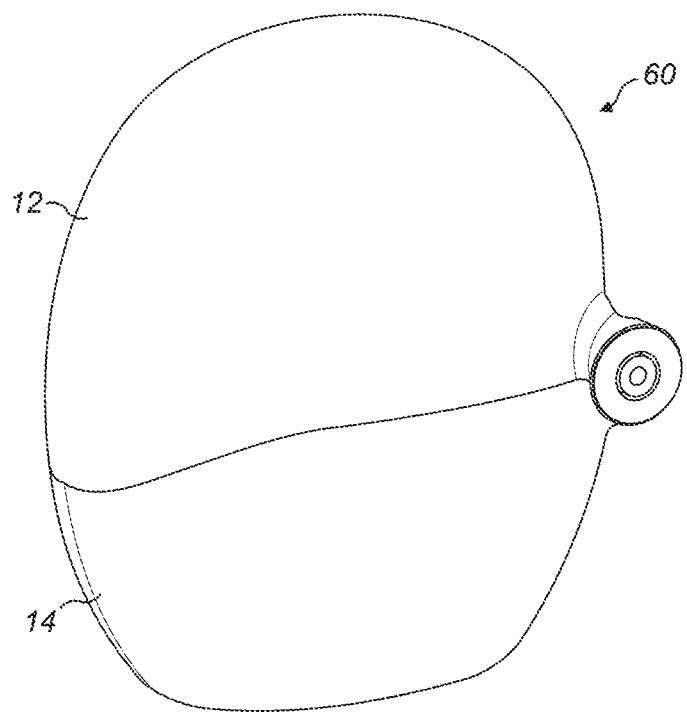
Figure 8:
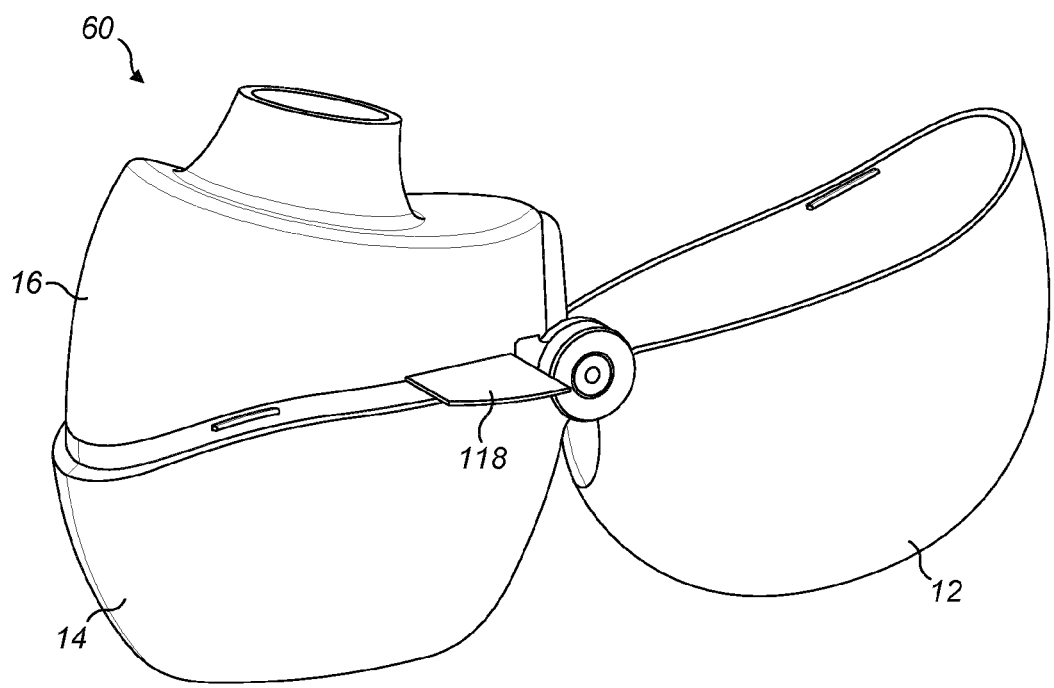

As with the first embodiment, a protective cap 12 covers the mouthpiece 16 when in a closed condition, as shown in FIG. 5, and reveals the mouthpiece 16 in an open condition, as shown in FIG. 8. For inhalation, the cap 12 is placed into its open condition. To prepare for inhalation, the mouthpiece 16 is moved such that the blister folding element 24 is placed into its first position, as explained previously.

Figure 6:
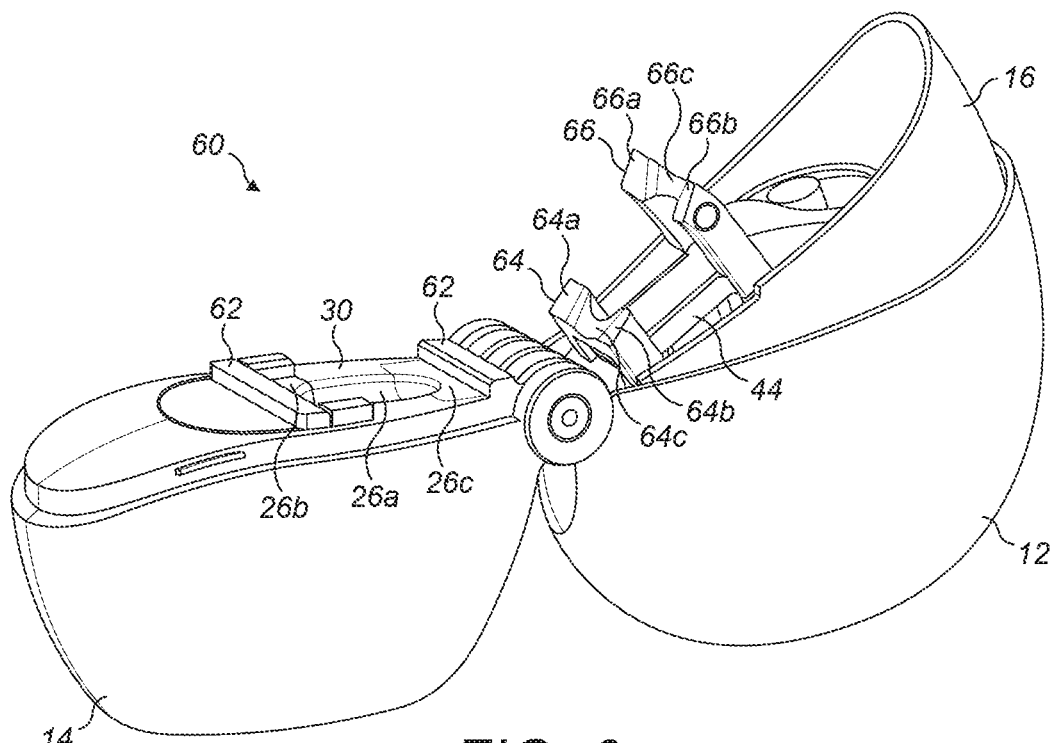
Figure 7:
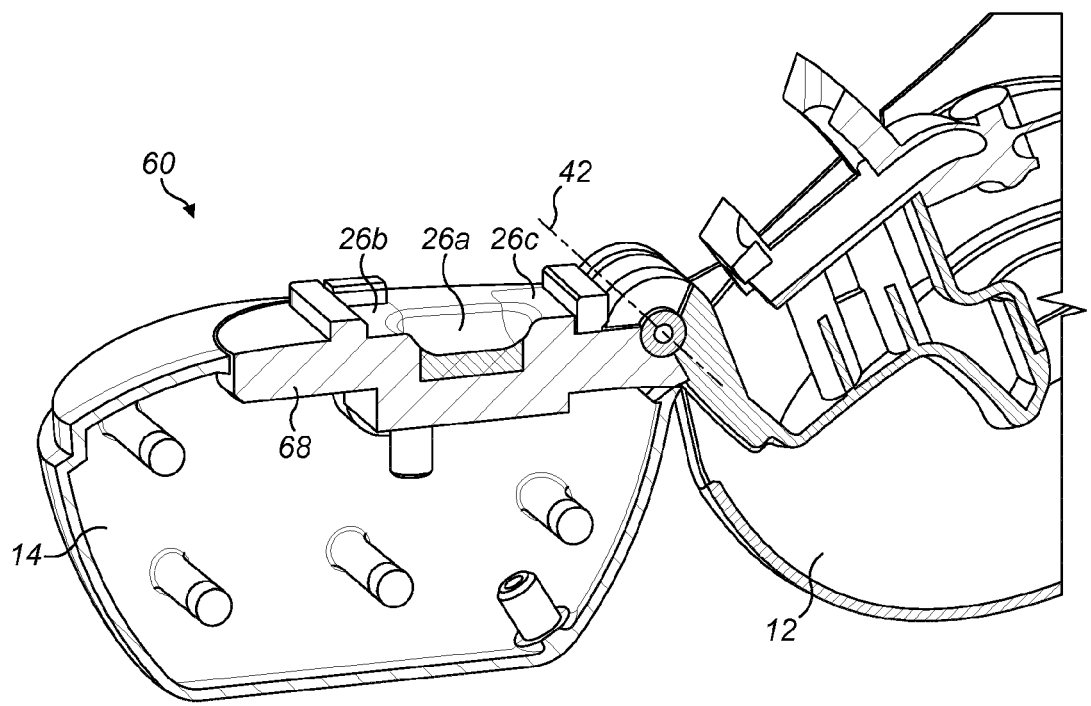

As best seen in FIGS. 6 and 7, the blister support element 20 is formed in and on an upper surface 38 of the housing 14. A tab stop 62 is located on the upper surface 38 of the housing 14 and is provided to prevent slippage of the blister 22 relative to the housing 14 during use. The blister seat 26 is recessed into the upper surface 38 of the housing 14 and is shaped for receiving an elongate blister bowl 28 of a blister 22. The blister seat 26 in this embodiment has a central portion 26a and two depressible end portions 26b, 26c, one either side of the central portion 26a. The blister support surface 30 is provided as part of the upper surface 38 of the housing 14, this being the housing surface extending between the blister seat 26 and the tab stop 62.

The blister folding element 24 comprises a pair of spaced apart fold members 64, 66 depending from a fold support structure 44. Each fold member 64, 66 is arch-like, having two fold feet 64a, 64b, 66a, 66b connected by an arcuate fold body 64c, 66c, the fold body 64c, 66c being intermediate the fold feet 64a, 64b, 66a, 66b. Each fold foot 64a, 64b, 66a, 66b has a bevelled free end. The first fold member 64 is shorter than the second fold member 66, when measured from the fold support structure 44. The fold member 64 situated nearest the pivotal axis 42 is shorter than the other fold member 66. The fold members 64, 66 are configured so as to be receivable within the voids created when the depressible portions 26b, 26c of the blister seat 26 are depressed.

Figure 10:
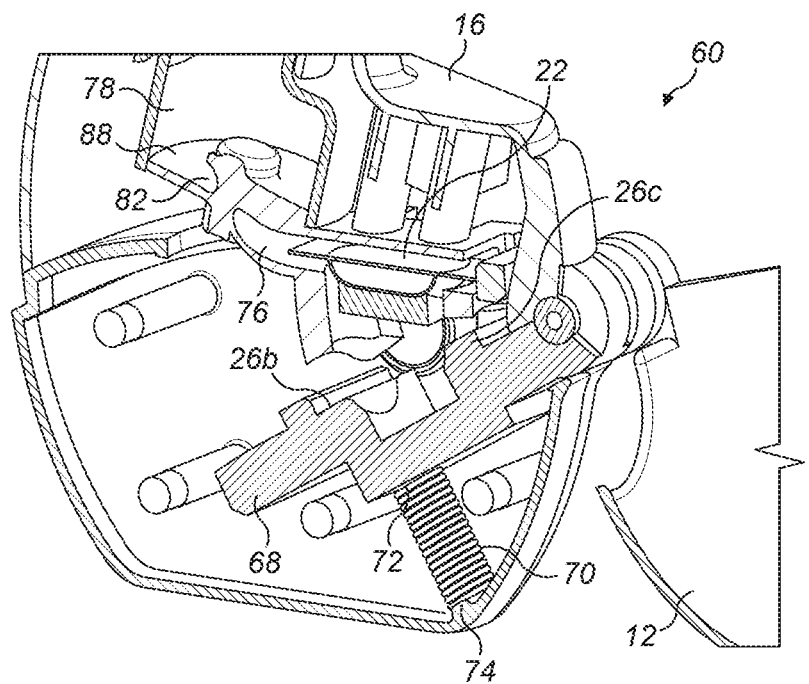

As can be seen in FIG. 10, the depressible portions 26b, 26c of the blister seat 26 are provided by a moveable first support arm 68, which is configured to co-operate or mate with the central portion 26a of the blister seat 26. The rigid first support arm 68 is pivotally connected at one end to the housing 14. The first support arm 68 pivots within the housing 14 about the same pivotal axis 42 as the cap 12 and the blister folding element 24.

When the first support arm 68 is in a rest position, the depressible portions 26b, 26c of the blister seat 26 are located adjacent to the central portion 26a of the blister seat 26. When the first support arm 68 is in an active position, the depressible portions 26b, 26c of the blister seat 26 are depressed relative to their initial rest position. In such a condition, the depressible portions 26b, 26c of the blister seat 26 are positioned away from the central portion 26a of the blister seat 26 and situated on an arcuate travel path about the pivotal axis 42.

A spring 70 is connected to an underside of the first support arm 68 at one end 72 and to an interior wall of the housing 14 at the other end 74. The spring 70 ensures that the first support arm 68 is biased towards its rest position.

In contrast to the blister support element 20 of the first embodiment, the blister support element 20 of the second embodiment is oriented differently with respect to the pivotal axis 42. In this embodiment, a longitudinal extent of the (untruncated) blister seat 26 is arranged perpendicularly relative to the pivotal axis 42 of the inhaler 60. In the first embodiment, the longitudinal extent of the (untruncated) blister seat 26 is arranged in parallel with the pivotal axis 42 of the inhaler 10 (see FIG. 1).

An airflow conduit 76 fluidly connects the blister opening device 18 with a cyclone chamber 78.

The cyclone chamber 78 is arranged within the mouthpiece 16. The chamber 78 is cylindrical and has a longitudinal axis 80 that extends between an airflow inlet 82 and an airflow outlet 84. The airflow inlet 82 is positioned at one end of the chamber 78 for the flow of drug laden air into the chamber 78 from a burst blister 22 and the airflow outlet 84 is positioned at an opposing end for the flow of drug laden air out of the mouthpiece 16 and into a patient's airway via orifice 85.

The longitudinal axis 80 of the chamber 78 is arranged at an acute angle relative to the plane 86 of the blister seat 26. Advantageously, this means that when a user places the inhaler to their mouth, the burst blister 22 is inclined to empty into the cyclone chamber 78 under gravity, even without inhalation. This contributes towards a higher emitted dose.

The chamber 78 has a spiraled floor 88, near or at the airflow inlet 82, to encourage a swirling airflow between the inlet 82 and the outlet 84 of the chamber 78.

Figure 9:
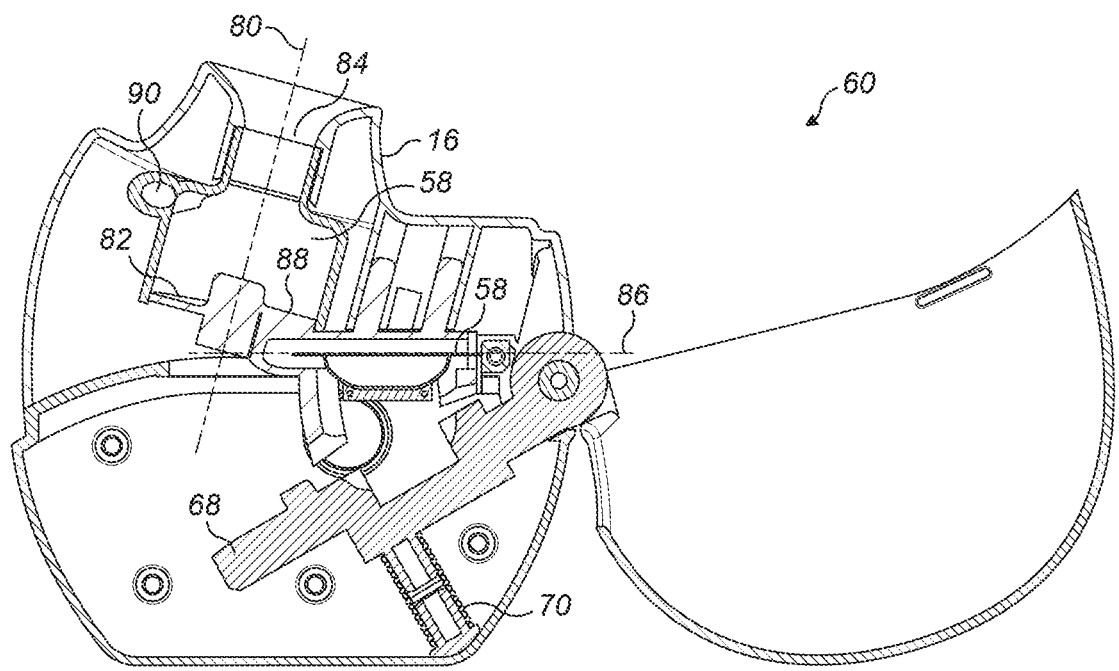

The chamber 78 comprises a bypass air inlet 90 for the flow of clean air into the chamber 78 to interact with the drug laden air flowing between the inlet 82 and the outlet 84. However, two or more bypass inlets could be provided. As shown in FIG. 9, the bypass air inlet 90 is arranged near the outlet 84. Also, the bypass air inlet 90 is arranged tangentially to the chamber 78 so that, in use, a cyclonic airflow is generated from clean air around the drug laden airflow. Further detail on the deagglomeration process that takes place within the cyclone is provided later.

This embodiment of the blister opening device 18 operates in a very similar manner to the first embodiment in so far as a blister folding element 24 is pivotable relative to a blister support element 20 between a first position, for insertion of a blister 22 into or onto the blister support element 20 and a second position in which the blister folding element 24 has co-operated with the blister support element 20. As the blister folding element 24 moves from the first position into the second position, the fold members 64, 66 urge against the depressible portions 26b, 26c of the blister seat 26, and the first support arm 68 is forced into the active position. Such movement causes the two portions of the blister 22 which overlie the depressible portions 26b, 26c to fold relative to the rest of the blister 22 and two openings 56a, 56b to form, in a similar manner to the first embodiment.

After use, the cap 12 is returned to its closed condition. The cap 12 is retained in its closed condition by virtue of a snap-fit engagement (not shown) of the cap 12 over the housing 14. An annular step is provided at a peripheral extent of the upper surface of the housing 14. A bead is arranged on an upper wall of the step, and protrudes radially outwardly. A protrusion extends around an inner wall of the cap 12, near the mouth of the cap 12 and protruding radially inwardly. The bead and the protrusion are co-operable together to produce the aforementioned snap-fit engagement of the cap 12 on to the housing 14.

As best seen in the demonstration rig 101 of FIGS. 11 A to E, the blister opening device 18 optionally comprises a stress concentrating means 102 for creating a stress concentration in the lid of the blister 22 immediately prior to the blister 22 being folded. The stress concentrating means 102 comprises a preferably circular piercing head 104 and two piercing teeth 106 depending therefrom. The piercing head 104 is connected to a resilient second support arm 110. The second support arm 110 is pivotally connected about a pivot point 112. In such an arrangement, the second support arm 110 passes through the fold support structure 44 such that the piercing head 104 extends between the two fold members 64, 66.

The stress concentrating means 102 is releasably engageable with the two fold members 64, 66. The stress concentrating means 102 is moveable between first, second and third positions.

In the first position, the piercing head 104 is engaged with each fold member 64, 66 at its distal end (see FIGS. 11 A and B). In the second position, the piercing head 104 is engaged mid-way up the fold members 64, 66 (see FIGS. 11 C and D). In the third position, the piercing head 104 is engaged with each fold member 64, 66 at its proximal end (see FIG. 11E).

The sequence of steps relating to the blister opening with pre-folding piercing is explained now with reference to FIGS. 11 A to E, FIGS. 12 A to D and FIGS. 13 A to C.

Figure 11A:
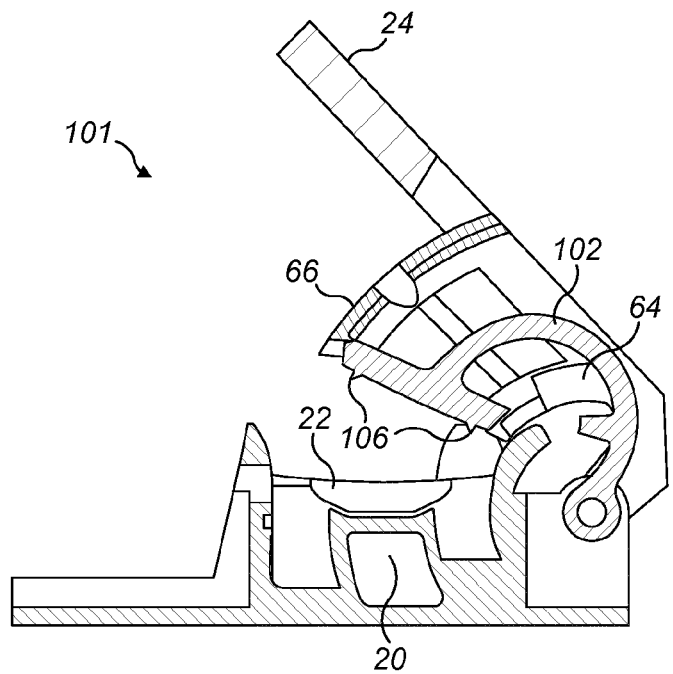
Figure 11B:
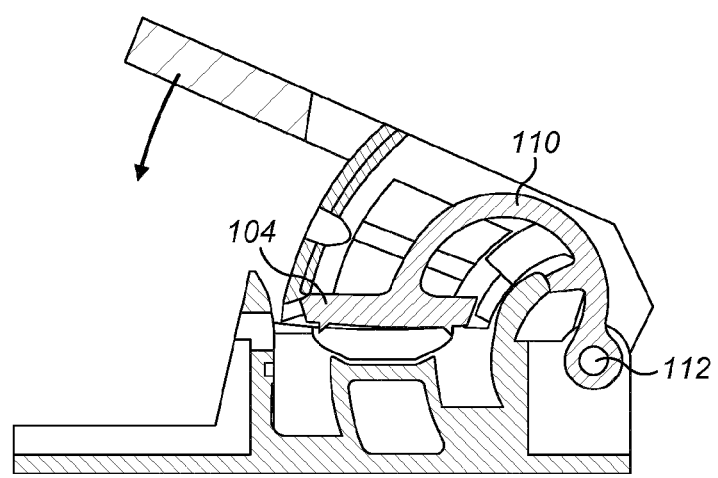
Figure 11C:
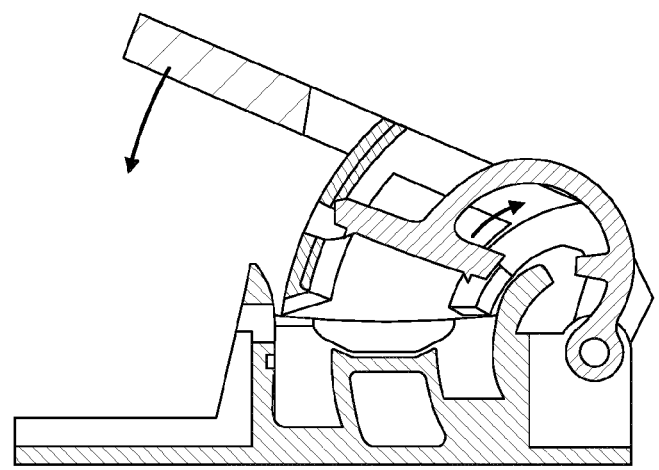
Figure 11D:
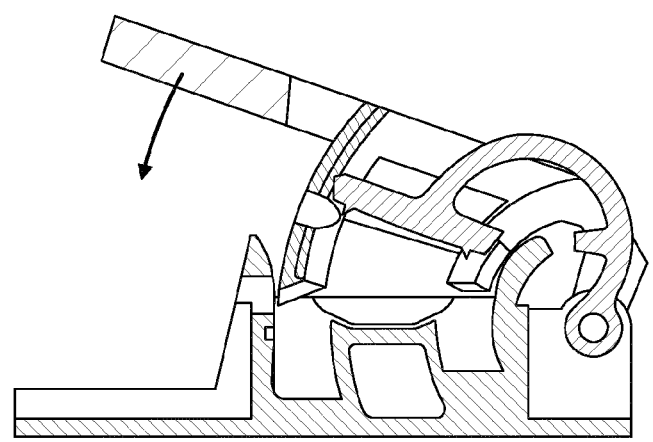
Figure 11E:
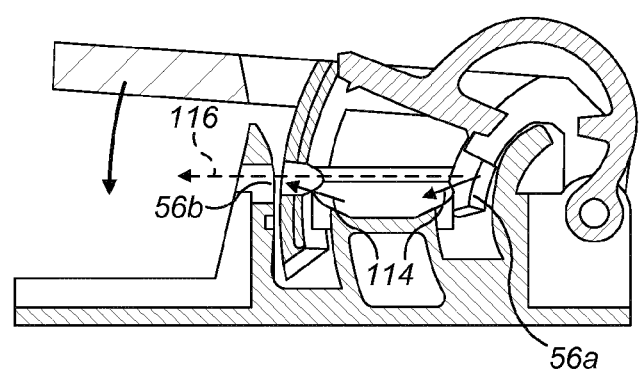
Figure 12A:
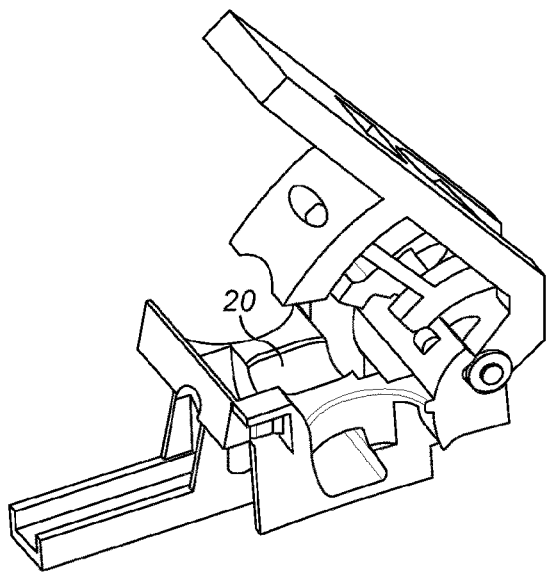
Figure 12B:
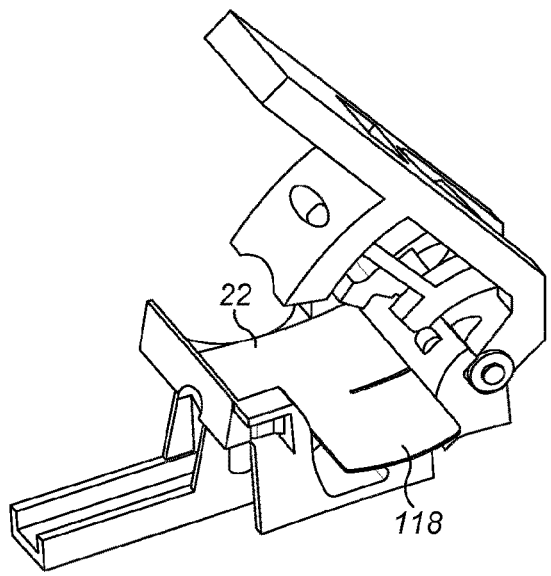
Figure 12C:
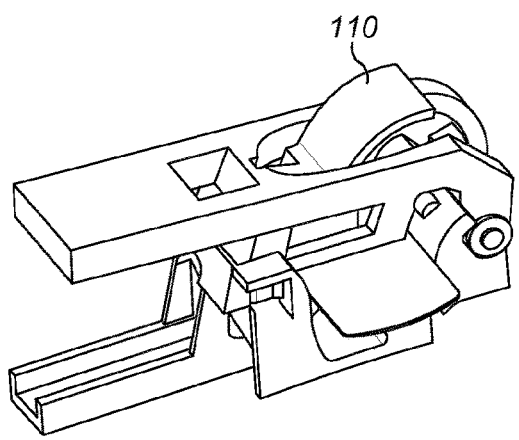
Figure 12D:
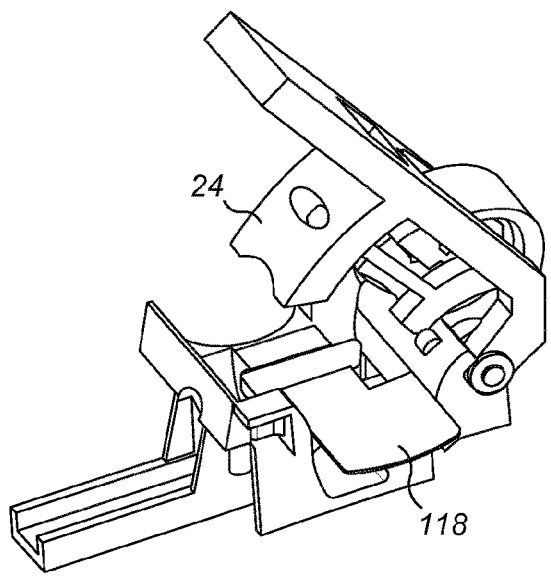
Figure 13A:
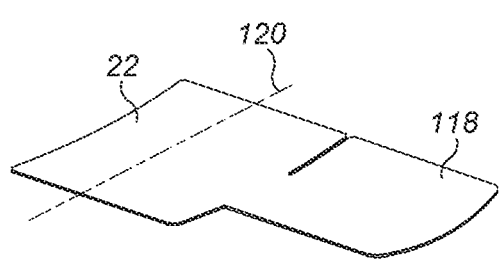
Figure 13B:
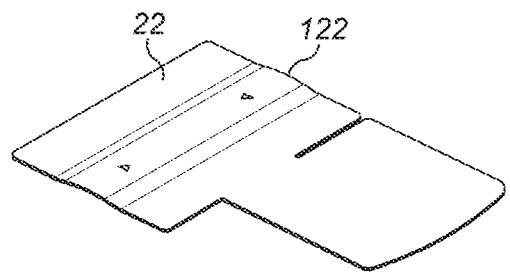
Figure 13C:
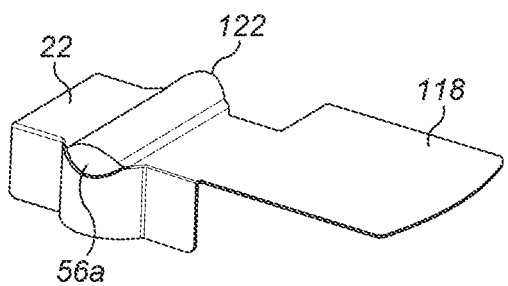

The blister opening device 18 is opened by pivoting the blister folding element 24 relative to the blister support element 20 (FIG. 12A);

A blister 22 (FIG. 13A) is inserted into the blister support element 20 (FIG. 11A, FIG. 12B);

The blister folding element 24 begins to move from the first position. The stress concentrating means 102 moves and makes contact with the blister 22 and pierces two small holes in the blister lid 54 (FIG. 11B);

Further movement of the fold members 64, 66 downwards overcomes the latch retaining the piercing head 104. The piercing head 104 moves up due to the energy in the resilient second support arm 110 (FIG. 11C);

After finally making contact with the blister 22, the initial movement of the fold members 64, 66 causes the blister to morph into the intermediate form of the blister 22, now with a curved upper surface (FIG. 11D, FIG. 13B);

Final movement of the fold members 64, 66 bursts open the blister 22 whilst forming the two large openings 56a, 56b at the end of the blister 22. An air path through the blister 22 via the two openings 56a, 56b, as indicated by the two short arrows 114 is now possible. It is at this point that the inhaler 60 is ready for inhalation (FIG. 11E, FIG. 12C, FIG. 13C); and The blister opening device 18 is opened once more by pivoting the blister folding element 24 relative to the blister support element 20, to reveal the used blister form (FIG. 12D).

The fold support structure 44 is adapted to provide a bypass air conduit 58 for the flow of clean air over the burst blister 22 when the blister folding element 24 is in the second position. This can be seen in FIG. 11E. A bypass airflow path through the bypass air conduit 58 is indicated by a dashed arrow 116.

Typically, the total airflow through the inhaler 60 to the user comprises 30% coming via the bypass air inlet(s) 90 on the cyclone chamber 78, 35% via the bypass air conduit 116 over the burst blister, and 25% through the actual burst blister 22 via the two openings 56a, 56b. Thus 70% of the airflow is from fresh air and 25% is powder laden air. The three airflow paths meet in the cyclone chamber 78 to promote deagglomeration of the cohesive agglomerates intended for use with this inhaler 60.

A blister 22 having a curved upper surface may be used in either of the two embodiments already described. The blister may include a conventional blister tab 118. The blister 22 may be curved along the longitudinal extent 120 of the blister bowl 28, as shown in FIG. 13A. Such a pre-curved blister 22 is advantageous as it means that the blister lid 54 will consistently pop upwards during blister opening. In the intermediate blister form, (FIG. 13B) the resultant formed blister is curved along the lateral extent of the blister bowl 28 (i.e. across the longitudinal extent of the blister bowl 28). In the final blister form (FIG. 13C), the curve 122 across the blister bowl 28 is increased and openings 56a, 56b are formed.

Alternatively, the blister may be curved about the lateral extent of the blister bowl 28.

Figure 14:
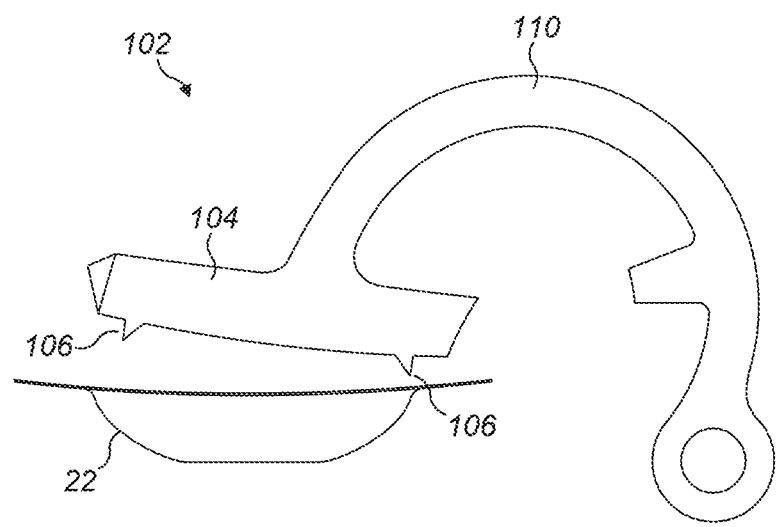

When the stress concentrating means 102 is intended for use with curved blisters, the piercing head 104 may be arcuate, as shown in FIG. 14. An arcuate or curving form, matching the curved profile of the blister, helps to retain the shape of the blister 22 during pre-folding piercing. Otherwise, when a piercing head with a flat lower surface is lowered onto a blister with a curved upper surface, the piercing head will push down onto the uppermost points of the blister lid, causing the lower central portion of the blister lid to pop upwards prematurely. The subsequent movement of the blister folding element relative to the blister support member does not then controllably open the blister as desired. Consequently, opening is less predictable.

The stress concentrating means 102 may be implemented into either of the two embodiments described herein.

With either of the embodiments described above, a traditional blister 22 may be used with a planar blister lid 54 and a blister bowl 28 (FIG. 15A). Optionally, a blister 22 may incorporate at least one indentation 124. This causes slight pre-tensioning of the blister lid 54, as indicated by the arrows in FIG. 15B. Alternatively or additionally, the blister lid 54 may be significantly pre-tensioned by compressing the blister 22 inwardly, as indicated by the arrows in FIG. 15C.

Although demonstration rigs 57, 101 have been used for the purpose of introducing certain features, it is fully intended that these features be implemented in either one or both of the two embodiments described herein.

In brief, the blister opening device provides a predictable and reliable way of accessing powdered medicament stored within a blister. It also contributes to improved emitted doses for relatively cohesive powders.

Turning now to FIGS. 16 to 23, deagglomeration of a cohesive powder within the chamber will now be described in more detail. As mentioned earlier, agglomerates are broken up by impact or collision with the internal surfaces of the cyclone chamber. Generating particle fines is unlikely to be achieved in a single impaction. These figures show a progression of how a single (isolated) large particle/agglomerate typically behaves in a cyclonic airflow and demonstrate how that with this particular configuration of chamber, the particle undergoes several collisions.

First arrow 126 shows the path that the particle will take to get to the position in the subsequent pair of figures. Second arrow 128 shows the path that the particle has taken to get to the position it is currently in. Third arrow 130 represents the particle and its velocity.

Figure 17A:
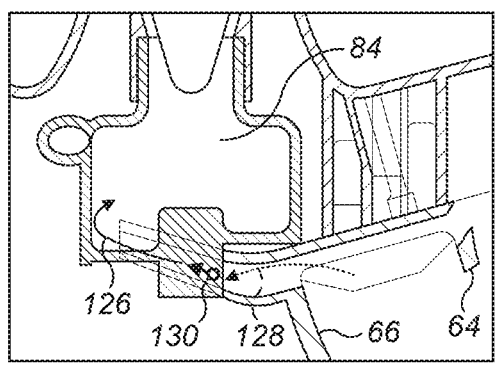
Figure 17B:
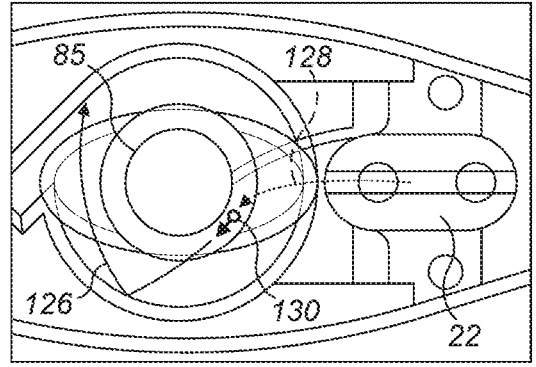
Figure 18A:
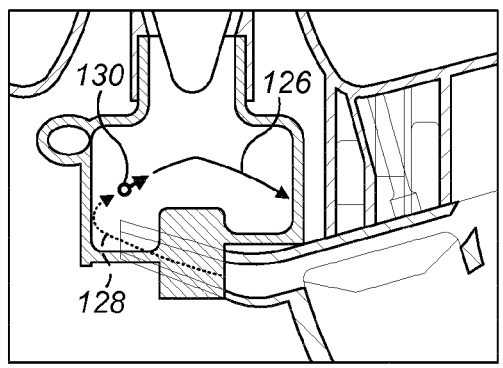
Figure 18B:
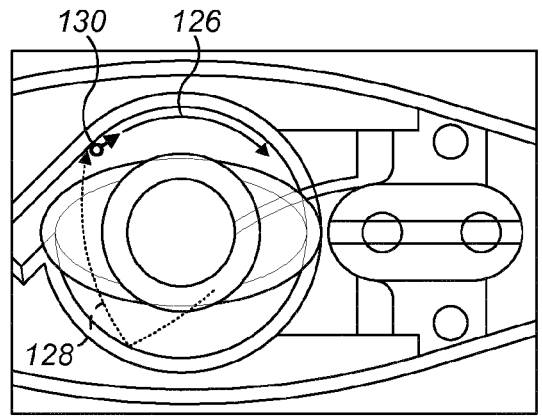
Figure 19A:
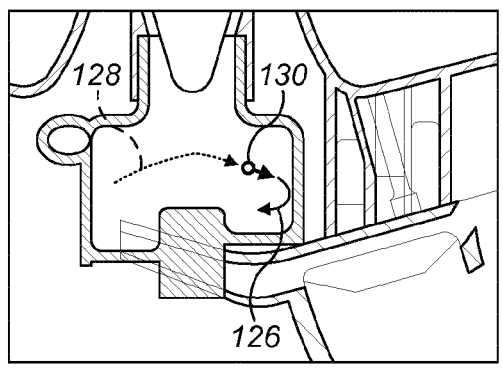
Figure 19B:
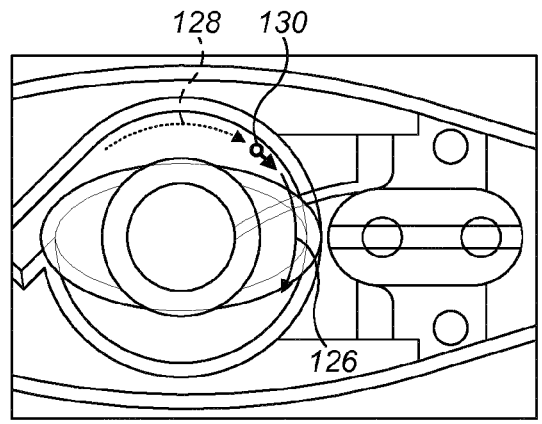
Figure 20A:
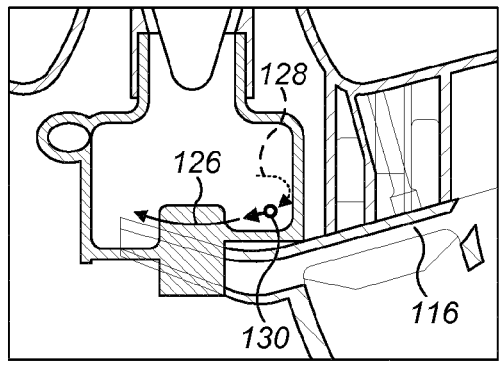
Figure 20B:
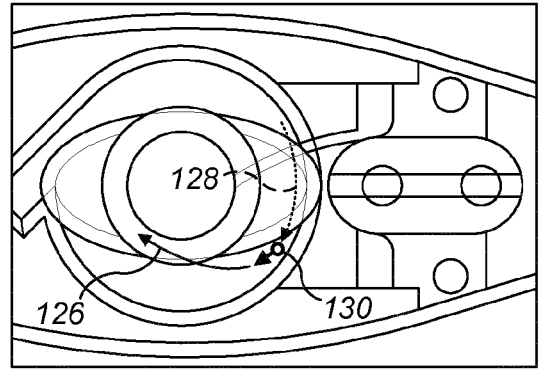
Figure 21A:
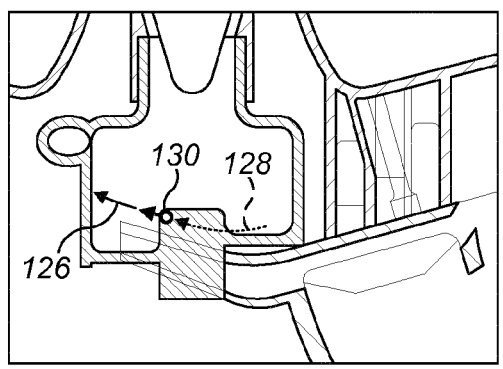
Figure 21B:
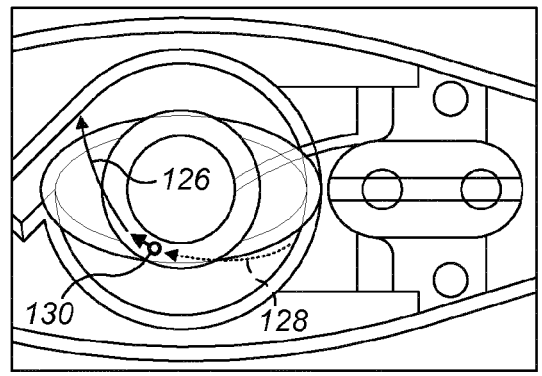
Figure 22A:
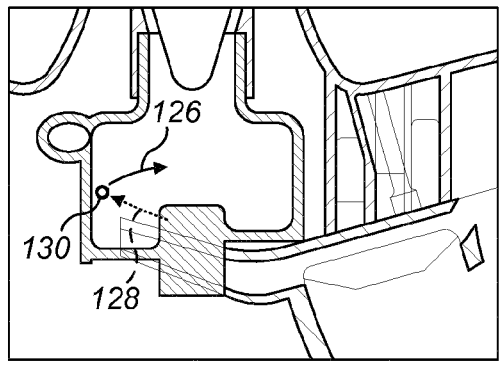
Figure 22B:
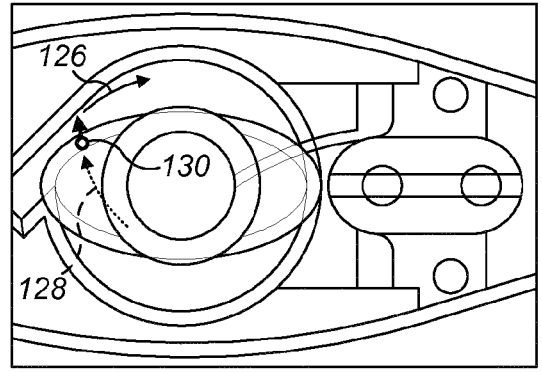
Figure 23A:
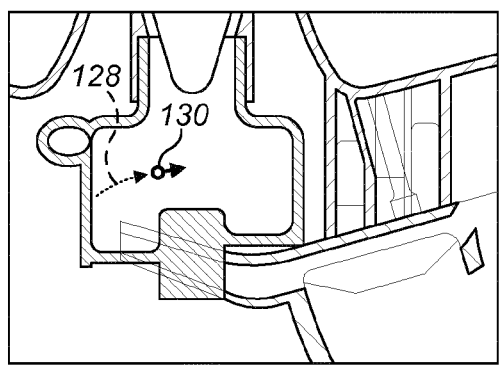
Figure 23B:
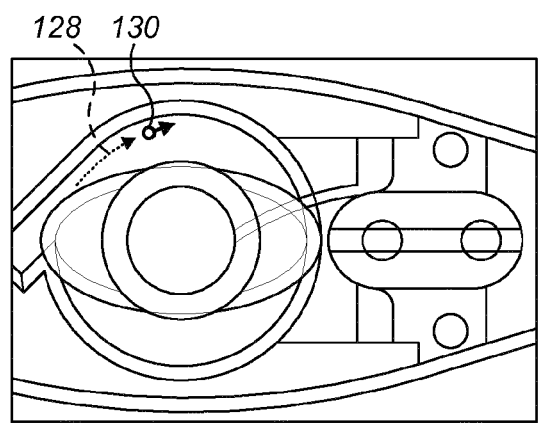

After the blister has been opened and upon initial inhalation by the user, the particle begins to travel out from the blister, as indicated in FIGS. 16A and 16B. The particle 130 passes into the airflow conduit 76, as indicated in FIGS. 17A and 17B. The particle 130 then moves though the chamber airflow inlet 82. Guided by the spiraled floor 88 of the chamber 78, the particle 130 immediately impacts the interior chamber wall, best seen in FIG. 17B. The particle 130 continues to travel in the inspiratory airflow towards the airflow outlet 84, and due to the earlier impact, is caused to traverse the chamber to then strike the chamber wall once again, as shown in FIGS. 18A and 18B. At this point, the particle 130 comes under the influence of the incoming airflow from the bypass air inlet(s) 90 and is forced downwards, back towards to the airflow inlet 82, as shown in FIGS. 19A and 19B and FIGS. 20A and 20B. This is why the location of the bypass air inlet(s) is so important as being at the top of the chamber, at or near the airflow outlet 84. When the particle 130 consequently strikes the spiraled floor 88, as seen in FIGS. 21A and 21B, the particle 130 begins to move back towards the airflow outlet 84 once more. Bypass airflow originating from the bypass air conduit 116 at the bottom of the chamber 78 contributes towards forcing the swirling airflow upwards and the particle 130 back towards the airflow outlet 84, as shown in FIGS. 22A and 22B and FIGS. 23A and 23B.

A trajectory such as the one described above is optimised when the bypass air cyclone(s) 90 is(are) used in conjunction with the spiraled floor 88 and the bypass airflow from the bypass airflow conduit 116. However, any combination of these three features offers benefits over known cylindrical chambers with a flat base.

This particle 130 is just one of many particles making up the powder coming from the opened blister. When the powder is seen acting in bulk, the finer particles tend to enter the chamber 78, and exit soon after with a minimal number of impactions, whereas the larger particles become drawn into repeating loops, incurring impaction after impaction until their inertia is such that they can escape from the chamber 78. Consequently, the residence time within the chamber 78 is much greater for the larger particles than for the finer particles. This significantly improves the fine particle fraction of the dose for cohesive formulations.

Many modifications and variations of the invention falling within the terms of the following claims will be apparent to those skilled in the art and the foregoing description should be regarded as a description of the preferred embodiments only.

The invention claimed is:

1. A dry powder inhaler comprising a housing to receive a single blister containing a dose of medicament for inhalation by a user, said blister comprising a blister lid attached to a blister bowl, said blister having a middle portion and two spaced apart portions, said blister bowl having a circumference, a mouthpiece through which the dose of medicament is inhaled by the user and a blister opening device, the blister opening device comprising a blister support element for supporting the middle portion of the blister containing the dose of medicament for inhalation by the user, and a blister folding element co-operable with the blister support element, the blister folding element and the blister support element being moveable relative to each other between a first position, for insertion of said middle portion of the blister into or onto the blister support element, and a second position in which the blister folding element has co-operated with the blister support element, movement from the first position to the second position causing the two spaced apart portions of said blister to fold relative to the middle portion of the blister along two respective fold lines and against the blister support element to produce two spaced apart openings, each opening extending along a portion of the circumference of the blister bowl, beginning and terminating at points located on the respective fold line such that, when the user inhales through the mouthpiece, an airflow through the blister via the two openings is generated to entrain the dose contained therein and carry the dose out of the blister and via the mouthpiece into the user's airway, wherein the blister folding element is not configured to cut, slice or pierce the blister, and wherein the two spaced apart openings are formed between the blister lid and the blister bowl and are formed by separation of the blister lid from the blister bowl.

2. The dry powder inhaler of claim 1, wherein the blister folding element and the blister support element are pivotally connected to each other about a pivotal axis.

3. The dry powder inhaler of claim 2, wherein the blister support element comprises a blister seat to support a blister bowl and a blister support surface to support a periphery of the blister surrounding said blister bowl.

4. The dry powder inhaler of claim 3, wherein the blister seat comprises a central portion which has a truncated oval shape, each fold line being one edge of truncation.

5. The dry powder inhaler of claim 4, wherein the blister seat further comprises two depressible end portions adjacent to and on either side of the central portion.

6. The dry powder inhaler of claim 4, wherein the blister seat is configured such that the fold lines are of different lengths.

7. The dry powder inhaler as claimed of claim 3, wherein a longitudinal extent of the blister seat is arranged in parallel with the pivotal axis.

8. The dry powder inhaler of claim 3, wherein a longitudinal extent of the blister seat is arranged perpendicularly to the pivotal axis.

9. The dry powder inhaler of claim 3, wherein the blister seat incorporates a raised feature to cause an indentation at the base of the blister for internally pressurising the blister.

10. The dry powder inhaler of claim 1, the blister folding element further comprising at least one pair of spaced apart fold members receivable into the blister support element, the at least one pair of spaced apart fold members extending from a fold support structure.

11. The dry powder inhaler of claim 10, wherein the at least one pair of spaced apart fold members comprises a first pair of fold members and a second pair of fold members, wherein the first pair of fold members is longer than the second pair of fold members.

12. The dry powder inhaler of claim 10, wherein a free end of each fold member is beveled.

13. The dry powder inhaler of claim 1, wherein the blister is curved along a longitudinal extent of the blister.

14. The dry powder inhaler of claim 13, the blister opening device further comprising a stress concentrating means to create a stress concentration in the lid of the blister prior to the blister being folded.

15. The dry powder inhaler of claim 14, wherein the stress concentrating means comprises a piercing head that is curved to match the profile of the curved blister.

16. A dry powder inhaler comprising a housing to receive a single blister containing a dose of medicament for inhalation by a user, said blister comprising a blister lid attached to a blister bowl, said blister having a middle portion and two spaced apart portions, said blister bowl having a circumference, a mouthpiece through which the dose of medicament is inhaled by the user and a blister opening device, the blister opening device comprising a blister support element for supporting the middle portion of the blister containing the dose of medicament for inhalation by the user, and a blister folding element co-operable with the blister support element, the blister folding element and the blister support element being moveable relative to each other between a first position, for insertion of said middle portion of the blister into or onto the blister support element, and a second position in which the blister folding element has co-operated with the blister support element, movement from the first position to the second position causing two spaced apart portions of said blister to fold relative to the middle portion of the blister along two respective fold lines and against the blister support element to produce two spaced apart openings, each opening extending along a portion of the circumference of the blister bowl, beginning and terminating at points located on the respective fold line such that, when the user inhales through the mouthpiece, an airflow through the blister via the two openings is generated to entrain the dose contained therein and carry the dose out of the blister and via the mouthpiece into the user's airway, wherein the blister folding element is not configured to cut, slice or pierce the blister, wherein the two spaced apart openings are formed between the blister lid and the blister bowl are formed by separation of the blister lid from the blister bowl, wherein the blister support element comprises a blister seat to support a blister bowl and a blister support surface to support the periphery of the blister surrounding said blister bowl, and wherein the blister seat further comprises two depressible end portions adjacent to and on either side of a central portion of the blister seat.

17. The dry powder inhaler of claim 16, wherein a longitudinal extent of the blister seat is arranged in parallel with the pivotal axis.

18. The dry powder inhaler of claim 16, wherein a longitudinal extent of the blister seat is arranged perpendicularly to the pivotal axis.

19. The dry powder inhaler of claim 16, wherein the blister seat incorporates a raised feature to cause an indentation at the base of the blister for internally pressurising the blister.

20. The dry powder inhaler of claim 16, the blister folding element further comprising at least one pair of spaced apart fold members receivable into the blister support element, the at least one pair of spaced apart fold members extending from a fold support structure.

* * * * *